United States Patent [19]

Chmielinski

[11] Patent Number: 5,022,394

[45] Date of Patent: Jun. 11, 1991

[54] HEAT AND MOISTURE EXCHANGER DEVICE FOR TRACHEOSTOMY PATIENTS

[75] Inventor: Mark A. Chmielinski, Troy, Mich.

[73] Assignee: HomeCare of Dearborn, Dearborn, Mich.

[21] Appl. No.: 463,851

[22] Filed: Jan. 12, 1990

Related U.S. Application Data

[63] Continuation of Ser. No. 255,520, Oct. 11, 1988, abandoned.

[51] Int. Cl.$^5$ .................. A62B 19/00; A61M 16/04
[52] U.S. Cl. .......................... 128/207.14; 128/206.17
[58] Field of Search ............... 128/207.14, 207.17, 128/206.17

[56] References Cited

U.S. PATENT DOCUMENTS

| | | | |
|---|---|---|---|
| 2,491,647 | 12/1949 | Colavita | 128/275 |
| 3,236,236 | 2/1966 | Hudson | 128/185 |
| 3,330,271 | 7/1967 | Hozier | 128/207.14 |
| 3,667,475 | 6/1972 | Venturelli et al. | 128/351 |
| 3,811,436 | 5/1974 | Ferrell | 128/207.17 |
| 3,824,999 | 7/1974 | King | 128/207.17 |
| 3,920,009 | 11/1975 | Olsen | 128/207.14 |
| 4,090,513 | 5/1978 | Togawa | 128/212 |
| 4,202,330 | 5/1980 | Jariabka | 128/204.18 |
| 4,263,921 | 4/1981 | Trugillo | 128/207.14 |
| 4,274,406 | 6/1981 | Bartholomew | 128/206.21 |
| 4,325,366 | 4/1982 | Tabor | 128/207.16 |
| 4,332,245 | 6/1982 | Boone | 128/207.17 |
| 4,462,400 | 7/1984 | Simons et al. | 128/207.16 |
| 4,478,215 | 10/1984 | Hanlon | 128/201.13 |
| 4,558,708 | 12/1985 | Labuda et al. | 128/207.14 |
| 4,582,058 | 4/1986 | Depel et al. | 128/207.17 |
| 4,649,913 | 3/1987 | Watson | 128/207.14 |
| 4,658,813 | 4/1987 | Jones | 128/207.14 |
| 4,763,645 | 8/1988 | Kapp | 128/207.14 |

FOREIGN PATENT DOCUMENTS 668771  8/1963  Canada ..................... 128/207.17

OTHER PUBLICATIONS

Laboratory Evaluation of Moisture Output of Seven Airway Heat and Moisture Exchangers by Richard D. Branson and James Hurst Respiratory Care, Sep. 87, vol. 32, No. 9, pp. 741-747.

Technical Bulletin by Pall Bio-Medical Inc. relating to a heat and moisture exchanger for general adult anesthesia.

*Primary Examiner*—Clifford D. Crowder
*Assistant Examiner*—Kimberly L. Asher
*Attorney, Agent, or Firm*—Gifford, Groh, Sprinkle, Patmore and Anderson

[57] ABSTRACT

A heat and moisturizing exchanger device for use by patients having permanent tracheostomies when inspiring gases directly from the atmosphere. The device has a collar adapted to be sealingly secured to the neck of a patient with a tracheal opening and having an aperture adapted to receive a replacable heat and moisture exchanger cartridge. The cartridge contains a roll of hygroscopically treated material which collects heat and moisture from expired gas to warm and humidify the gas subsequently inspired by the patient. A nipple is provided for connetion to an auxiliary source of oxygen.

6 Claims, 1 Drawing Sheet

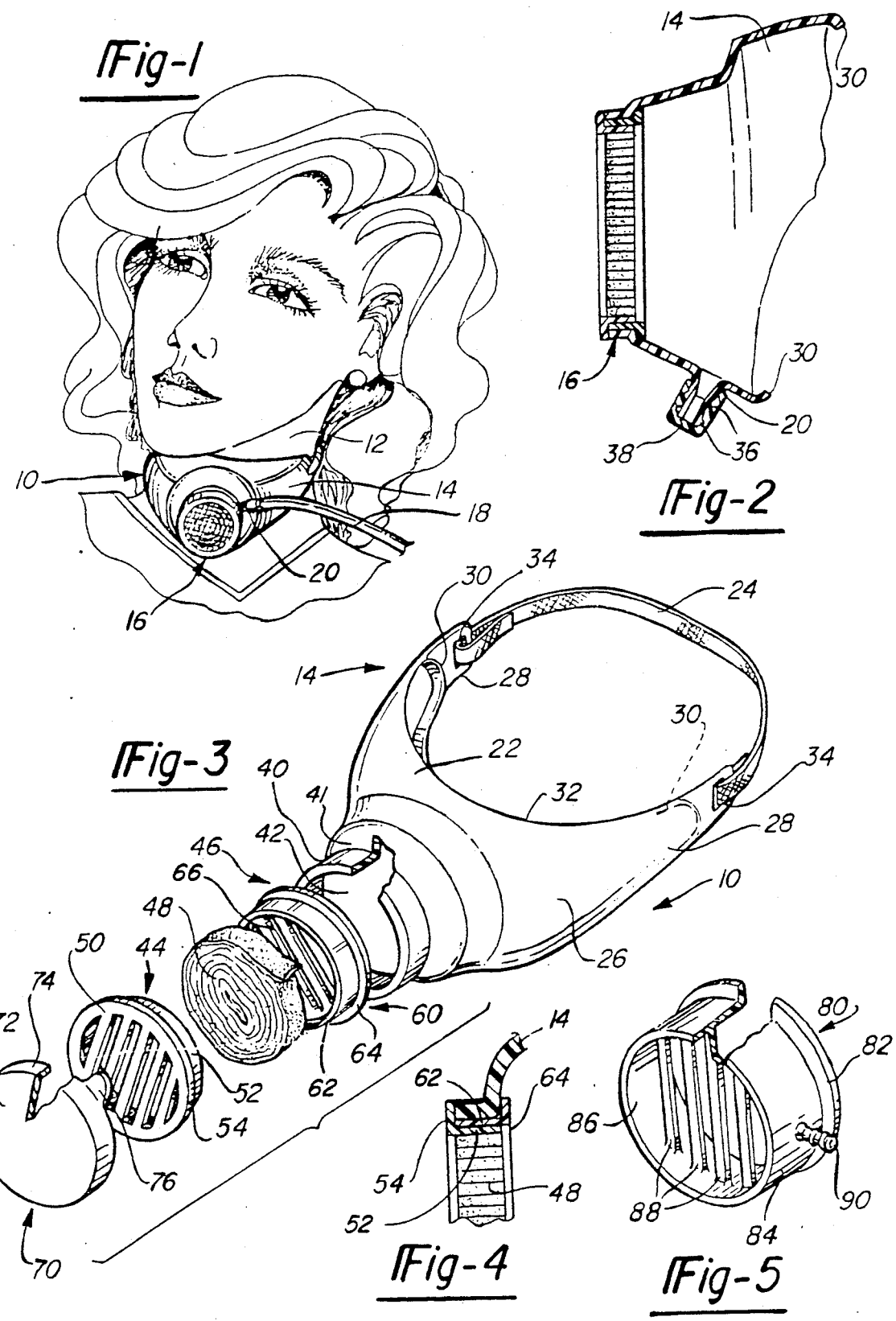

HEAT AND MOISTURE EXCHANGER DEVICE FOR TRACHEOSTOMY PATIENTS

This is a continuation of application Ser. No. 255,520, filed on Oct. 11, 1988, now abandoned.

FIELD OF THE INVENTION

This invention relates to an apparatus for patients having tracheostomies, and in particular to a device having a collar having a replacable heat and moisturizing exchanger cartridge.

DESCRIPTION OF THE PRIOR ART

Tracheal collars or masks for patients having connectors for attaching tracheostomies to oxygen hoses are known, such as disclosed in U.S. Pat. No. 3,236,236 to Hudson. Hudson discloses a mask suitable for wearing about the neck of the patient and having a rear flange portion for sealingly engaging the neck of the patient. A tubular adapter is mounted in the mask for accepting a hose connected to a device that delivers aerosols and/or a supply of oxygen. In this manner, aerosolized oxygen is provided through the hose and mask to the tracheal opening and lungs of the patient.

It is also known as disclosed by U. S. Pat. No. 4,090,513 to Togawa to provide a heat and moisture exchanger (HME) in line with the hosing from an oxygen supply. Such devices are used to warm and humidify the gases inspired by patients using artificial respirators. It is also known as disclosed by Branson and Hurst in "Laboratory Evaluation of Moisture Output of Seven Airway and Heat Moisture Exchangers", Respiratory Care, September, 1987, Volume 32, No. 9, page 741, to place a HME or artificial nose between an endotracheal tube and the patient-y of the ventilator circuit to collect heat and moisture from the patient's respiratory tract in the HME. During the subsequent inspiration, the collected heat and moisture warm and humidify the cold dry gas inpired by the patient.

Frequently, patients with tracheostomies are not required to continuously be connected to a supply of oxygen. These patients inspire gases directly from the atmosphere. Since the warming and humidifying functions of the nose are bypassed because of the tracheostomy, these patients require supplemental humidification. Thus, it would be desirable to provide a HME which could be utilized to heat and humidify gas drawn from the atmosphere when the patient is not connected to an oxygen supply. It would also be desirable to provide a HME which would be compact and which could be easily hidden from view to warm and humidify the gas inspired by the patients.

SUMMARY OF THE INVENTION

Accordingly, a primary object of the invention is to provide a compact HME device for use by patients with tracheostomies when inspiring gases directly from the atmosphere. In order to accomplish this and other objects of the invention, Applicant disloses a collar adapted to be sealingly secured to the neck of the patient over the tracheal opening and having an aperture adapted to receive a replaceable heat and moisture exchanger cartridge. The cartridge has a front casing and a rear casing which are mated together to form a thin sandwich about a roll of hygroscopically treated material. Each cartridge has a plurality of openings to permit the passage of gas from the atmosphere through the hygroscopically treated material for heating and humidifying the gas to be inspired. The cartridge is provided with a pair of surfaces to securely position the cartridge. The cartridge is adapted for ready removal and replacement when necessary.

The collar may also be provided with a nipple on the cartridge for connection with a standard oxygen supply tubing. A cap is provided to seal the nipple when not connected to the tubing.

Thus, Applicant discloses a HME device for tracheostomy patients (particularly for patients having permanent metal tracheostomies) for use when inspiring gas from the atmosphere. The device has a cartridge which may be readily removed and replaced. The device has a thin cross-section so it may be easily covered by the patient during use. In this way, the patient may freely move without being tethered to an oxygen or aerosol hose. The HME device reduces heat and water loss via the bronchpulmonary tree and provides passive humidification to preserve tracheal cellular morphology.

Other objects and advantages of the invention will be apparent from a reading of the following detailed description.

BRIEF DESCRIPTION OF THE DRAWING

FIG. 1 is a perspective view of a heat and moisture exchanger device according to the invention positioned on the neck of a patient;

FIG. 2 is a sectional view of the collar with a HME cartridge according to the invention;

FIG. 3 is an exploded perspective view showing the collar, HME cartridge and cover according to the invention;

FIG. 4 is a partial side view of the HME cartridge; and

FIG. 5 is a perspective view of an alternative embodiment of a HME cartridge according to the invention.

DETAILED DESCRIPTION OF THE PREFERRED EMBODIMENTS

As best shown in FIG. 1, a heat and moisture exchanger device 10 for warming and humidifying air from the atmosphere is positioned on the neck 12 of a patient having a tracheostomy (not shown). The exchanger device 10 has a collar 14 bearing a heat and moisture exchanger (HME) cartridge 16. Also shown is an oxygen hose 18 connected to a nipple 20 to provide an auxiliary supply of oxygen.

As best shown in FIG. 3, the collar 14 has a body 22 formed of a suitable soft flexible elastomeric material which is held in position by a strap 24. The body 22 has an outwardly bulged forward wall 26 defining a chamber and a pair of tabs 28 extending rearwardly from the forward wall 26. An inwardly curving crescent-shaped flange 30 at a rear peripheral edge 32 of the body extends along an inner surface of each of the pair of tabs 28 to form a continuous gasket for engaging the neck of the patient. The inwardly curving flange 30 is formed integrally with the body of the same material with a thinner wall thickness. The flange is very flexible to conform to the neck and form a seal between the neck and collar. However, it is not necessary to have an airtight seal.

Each of the pair of tabs 28 extends rearwardly from the forward wall along the neck. A slot 34 is formed near the end of each tab to accept the ends of a strap 26 for encircling the neck. That strap is formed of elastic material. The ends of the strap 36 may be affixed to the tabs in any suitable manner, such as looping the strap through the slots 34 and tying or stitching the strap to itself. Alternatively, a strap and tabs may be provided with snaps or clips (not shown) to provide easy attachment of the strap to the tabs. The strap 26 extends behind the back of the neck of the patient to hold the collar snuggly in position over the tracheostomy (not shown).

The cylindrical nipple 20 extends outwardly from the body in a direction away from the neck of the patient for attachment of the hose 18 to provide a supply of oxygen from a tank (not shown) in the event that the patient should need oxygen. The nipple is provided with a pair of annular ridges 36 to hold the hose 18 or a cap 38 in place. When the hose 18 is not connected to the nipple 20, the cap is sealingly positioned over the nipple 20 to prevent any gas from the atmosphere from entering through the nipple. A cover 70 may be positioned over the cartridge when the device is not being used.

A tubular sleeve 40 extends outwardly from a flat portion 41 of the forward wall to define an opening 42 for mounting the HME cartridge 16. The opening 42 is positioned opposite the tracheostomy. In the preferred embodiment, the sleeve extends outwardly approximately ¼ of an inch. The sleeve is integrally formed with the body and is deformable to permit insertion of the cartridge 16.

The HME cartridge 16 is formed of a heat and moisture exchanger (HME) material sandwiched in a chamber formed between a front casing 44 and a rear casing 46. The casings are formed of suitable elastomeric material. The HME material may be of any suitable material for adding heat and humidity to gases expired during ventilation. In the preferred embodiment, the HME material is a hygroscopically treated paper roll 48, such as used in the Humid-Vent artificial nose marketed by Portex. The paper roll 48 is corrugated to provide axially aligned passages for the gas. As gas is expired from the patient, heat and humidity is trapped in the exchanger material so that gas which is subsequently inspired is instantaneously heated and humidified as it passes through the paper roll. The paper roll 48 is dimensioned to fill the chamber of the cartridge. Other suitable HME materials are set forth in the Branson and Hurst article cited above. Additionally, bacterial filtration may be accomplished by use of a hydrophobic filter medium such as utilized in the Pall HME reorder No. 22-22 manufactured by Pall Biomedical, Inc. of Fajardo, P.R.

The front casing 44 has a flat disc portion 50 and a cylindrical inner flange portion 52 extending outwardly from the disc portion. The inner flange portion 52 is positioned inwardly from the circumferential edge of the disc 50 to form an outer annular surface 54 for a purpose set forth below. A plurality of slotted openings 56 are formed in the disc portion to permit passage of gas from the atmosphere through the exchange material. The plurality of openings may be of any suitable size and shape to permit the passage of the gas while retaining the roll 48 in position.

The rear casing 46 is formed to mate with the front casing 44. The rear casing has a disc portion 60 with an outer flange portion 62 extending from the disc portion. The disc portion extends outwardly beyond the outer flange portion to form an annular inner surface 64. A plurality of openings 65 are formed in the disc portion to permit gas to pass from the exchanger into the chamber of the collar and then through the tracheostomy. The inner diameter of the outer flange portion of the rear casing is slightly smaller than the outer diameter of the inner flange portion 52 of the front casing. The inner and outer flange portions of the front casing and rear casing have equal axial length which are generally equivalent to the axial length of the sleeve 40.

As shown in FIG. 4, the cartridge is formed by press-fitting the outer flange 62 of a rear casing over the inner flange 52 of the front casing with the paper roll 48 positioned inside the chamber formed within the casings. In this way, the cartridge 16 is formed having a thin cross-section.

The cartridge 16 is inserted in the opening of the collar 14. The cylindrical sleeve 40 of the collar, being formed of flexible material, may be manipulated over the inner surface of the cartridge so that the sleeve 40 is positioned between the inner and outer annular surfaces of the cartridge, with the sleeve 40 contacting the outer flange 62 of the rear casing. The cartridge may be easily removed by snapping the cartridge out of the collar and be replaced by another cartridge when necessary because of deterioration of the filter medium or clogging of the exchanger material.

The cover 70 is adapted to snap tightly over the cartridge when the device is not being used. The cover has a flat portion 72 and a cylindrical portion 74 extending from the flat portion 72. A tab 76 extends from the flat portion 72 for removal of the cover. The cylindrical portion 74 of the cover 70 has an inner diameter adapted to snuggly receive the cartridge 70 and cylindrical sleeve 40. Thus, the cover may be positioned over the cartridge when the device has been removed from the patient.

An alternative embodiment of a rear casing 80 of the cartridge is shown in FIG. 5. The rear casing is provided with a rear annular surface 82 and a cylindrical portion 84 defining an opening 86. A plurality of bars 88 extend across the opening. The bars are spaced inwardly from a front edge of the rear casing to form a support to hold the HME material in place in the opening 86. A nipple 90 is positioned between the bars 88 and the annular surface to extend outwardly from the cylindrical portion 84. The nipple is spaced from the annular surface a distance equal to the length of the tubular sleeve 40 of the collar to permit insertion of the sleeve between the annular surface and the nipple. The nipple 90 is positioned between the plurality of bars 88 and annular surface 82 to permit oxygen to flow into the chamber of the collar without restriction from the HME material. The nipple is adapted to be connected to the oxygen/aerosol hose 18. The cartridge is formed in a sandwich, in the manner set forth above, with the front casing 44 (shown in FIG. 3) pressed fit to the rear casing 80. The rear casing may be formed of a suitable material such as an elastomer. In this embodiment, the nipple 90 for the hose is positioned directly on the cartridge and no nipple is formed on the collar.

Other configurations of the invention are contemplated, such as forming the cartridge with attachment members formed for attachment in trachael collars currently produced for connection with oxygen hoses. Such cartridges would be dimensioned to be positioned in an aperture of the collar.

The foregoing is considered as illustrative only of the principles of the invention. Since numerous modifications and changes will readily occur to those skilled in the art, the invention is not limited to the exact construction to operation shown and described. It is contemplated that the cartridge could be formed with a screen or lattice to provide the passage of gas through the cartridge. Accordingly, all suitable modifications may be resorted to, as falling within the scope of the invention.

I claim:

1. A device for humidifying and heating gas inspired from the atmosphere for use by a patient having a tracheostomy, said device comprising:

a collar having a front portion and a flange defining a chamber, said front portion having an aperture opposite the tracheostomy, said aperture being coaxial with the tracheostomy said flange sealingly engaging the neck of the patient;

means for securing said collar to the neck of the patient;

a replaceable cartridge removably mounted in said aperture of said collar, said cartridge having a heat and moisturizing member spaced apart from the tracheostomy and coaxial with the tracheostomy whereby heat and moisture collected from air expired from the patient are communicated to air inhaled by the patient, said cartridge being mounted within said collar adjacent said tracheostomy whereby said collar provides a compact profile which may be easily covered by the patient;

said cartridge having a pair of spaced apart radially extending flanges, said pair of flanges engaging said collar adjacent said aperture whereby said cartridge is removably mounted within said aperture for replacement with a similar cartridge;

wherein said collar has a nipple in communication with said chamber, said nipple adapted to be connected to a hose communicating oxygen from a supply of oxygen to said chamber for inspiration by a patient wearing said collar.

2. The device of claim 1 wherein said heat and moisturizing member comprises a roll of hygroscopically treated paper.

3. The device of claim 1 wherein said collar further comprises a sleeve extending outwardly from a flat portion, said sleeve defining said aperture.

4. The device of claim 1 wherein said means for securing comprises an elastic strap.

5. The device of claim 1 wherein said cartridge further comprises a front casing and a rear casing being pressed-fit together.

6. The device of claim 1 wherein said cartridge has a front casing and a rear casing, each of said front and rear casings having a plurality of openings for communicating gas to said heat and moisturizing member.

* * * * *